US008771609B2

(12) United States Patent
Ehben et al.

(10) Patent No.: US 8,771,609 B2
(45) Date of Patent: Jul. 8, 2014

(54) MODULE FOR PROCESSING A BIOLOGICAL SAMPLE, BIOCHIP KIT, AND USE OF THE MODULE

(75) Inventors: Thomas Ehben, Weisendorf (DE); Walter Gumbrecht, Herzogenaurach (DE); Manfred Stanzel, Erlangen (DE); Christian Zilch, Leipzig (DE)

(73) Assignee: Siemens Aktiengesellschaft, Munich (DE)

( * ) Notice: Subject to any disclaimer, the term of this patent is extended or adjusted under 35 U.S.C. 154(b) by 1048 days.

(21) Appl. No.: 11/653,230

(22) Filed: Jan. 16, 2007

(65) Prior Publication Data

US 2007/0166192 A1   Jul. 19, 2007

(30) Foreign Application Priority Data

Jan. 17, 2006   (DE) .......................... 10 2006 002 258

(51) Int. Cl.
*B01L 3/00* (2006.01)
(52) U.S. Cl.
USPC ............. 422/501; 422/50; 422/500; 422/502; 422/503; 422/504; 436/180
(58) Field of Classification Search
USPC ............. 422/99–100, 500–504, 50; 241/1–2; 436/180
See application file for complete search history.

(56) References Cited

U.S. PATENT DOCUMENTS

| | | | | |
|---|---|---|---|---|
| 3,715,189 A * | 2/1973 | Nighohossian et al. | ...... | 422/413 |
| 4,072,275 A | 2/1978 | Bartels et al. | | |
| 4,665,034 A * | 5/1987 | Chandler | ................... | 435/287.2 |
| 4,720,285 A * | 1/1988 | Pickhard | ...................... | 604/192 |
| 4,786,471 A * | 11/1988 | Jones et al. | ..................... | 422/61 |
| 4,828,395 A | 5/1989 | Saito et al. | | |
| 4,859,336 A * | 8/1989 | Savas et al. | ................ | 210/416.1 |
| 5,585,007 A * | 12/1996 | Antanavich et al. | .......... | 210/782 |
| 5,849,505 A * | 12/1998 | Guirguis | ....................... | 435/7.2 |
| 6,403,367 B1 | 6/2002 | Cheng et al. | | |
| 6,543,928 B2 * | 4/2003 | Beebe | ........................... | 366/144 |
| 6,544,734 B1 | 4/2003 | Briscoe et al. | | |
| 6,905,612 B2 * | 6/2005 | Dorian et al. | ................. | 210/806 |
| 7,077,175 B2 * | 7/2006 | Yin et al. | ........................ | 141/67 |
| 2002/0182718 A1 * | 12/2002 | Malmquist | ................. | 435/287.2 |

(Continued)

FOREIGN PATENT DOCUMENTS

DE   26 45 622         2/1979
DE   41 24 778 A1     1/1993

(Continued)

OTHER PUBLICATIONS

Great Britain Search Report dated May 14, 2007.

(Continued)

*Primary Examiner* — Jyoti Nagpaul
(74) *Attorney, Agent, or Firm* — Harness, Dickey & Pierce, P.L.C.

(57) ABSTRACT

A module for processing a biological sample for an analysis test is disclosed. The processing module includes, in at least one embodiment, an interface at which the processing module can be connected to a cartridge with a lab-on-a-chip, in which cartridge the analysis steps are carried out. A biochip kit is also disclosed. In at least one embodiment, the biochip kit includes one or more processing modules which are intended for different sample materials and which can be connected to the same cartridge type.

20 Claims, 4 Drawing Sheets

(56) References Cited

U.S. PATENT DOCUMENTS

| | | |
|---|---|---|
| 2004/0157343 A1 | 8/2004 | Sandell |
| 2004/0200909 A1* | 10/2004 | McMillan et al. ............ 241/1 |
| 2005/0070010 A1 | 3/2005 | Laurell et al. |
| 2005/0105077 A1 | 5/2005 | Padmanabhan et al. |
| 2006/0222569 A1 | 10/2006 | Barten et al. |
| 2006/0234243 A1 | 10/2006 | Bestmann |

FOREIGN PATENT DOCUMENTS

| | | |
|---|---|---|
| DE | 197 00 364 A1 | 7/1998 |
| DE | 103 19 045 A1 | 12/2004 |
| DE | 102006024149 | 11/2006 |
| EP | 1 221 340 A1 | 7/2002 |
| GB | 2 416 030 A | 1/2006 |
| WO | WO 03/104772 | 12/2003 |
| WO | WO 2005/007882 A2 | 1/2005 |
| WO | WO 2005/011867 | 4/2005 |
| WO | WO 2006/032044 | 3/2006 |

OTHER PUBLICATIONS

British Office Action dated Nov. 15, 2010 in corresponding Application No. GB0700586.1.

* cited by examiner

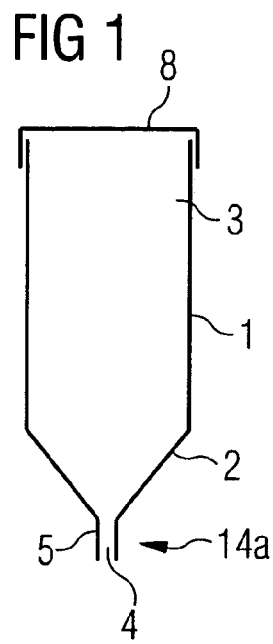
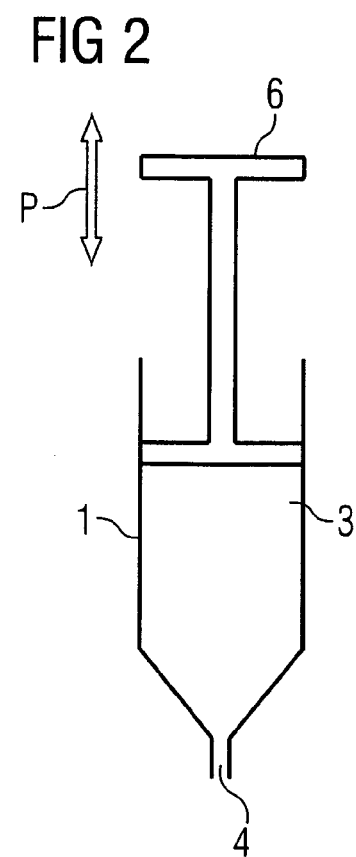
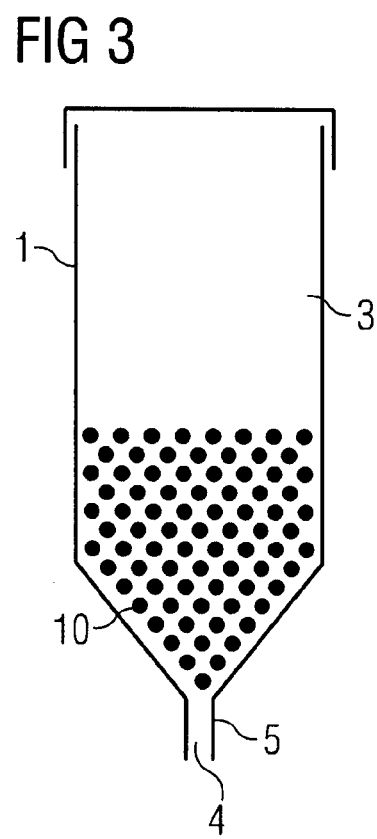

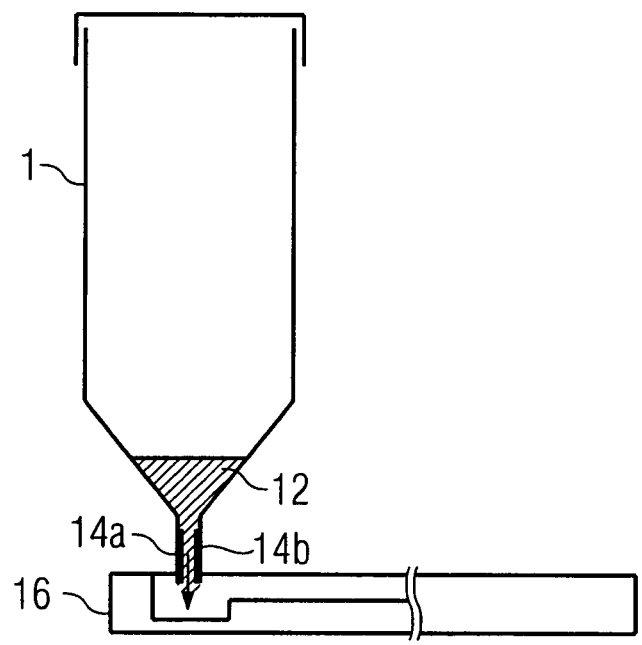
FIG 4
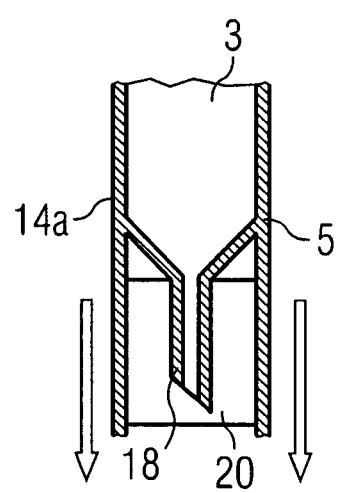
FIG 5
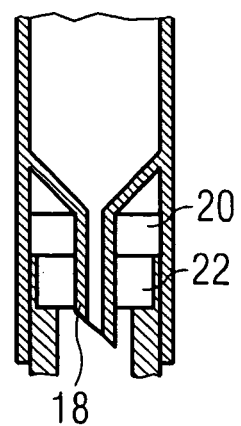
FIG 6
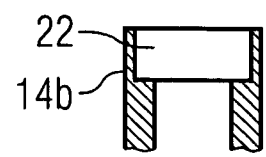

MODULE FOR PROCESSING A BIOLOGICAL SAMPLE, BIOCHIP KIT, AND USE OF THE MODULE

PRIORITY STATEMENT

The present application hereby claims priority under 35 U.S.C. §119 on German patent application number DE 10 2006 002 258.0 filed Jan. 17, 2006, the entire contents of which is hereby incorporated herein by reference.

FIELD

Embodiments of the present invention generally relate to a module for processing a biological sample. For example, it may relate to one for a test, in which a target substance in the sample is to be detected or quantified, where one or more processing steps can be carried out in the module. Embodiments of the invention are also generally directed at a biochip kit that contains one or more processing modules of this kind.

BACKGROUND

In numerous tests, particularly in diagnostic tests, certain target substances in a biological sample, in particular in a tissue sample or a body fluid, are to be detected. The target substances are, for example, certain cells such as viral or bacterial pathogens, or specific proteins or nucleic acids of a cell type, tissue type or organism.

For routine clinical practice, systems are desirable in which all the processing and analysis steps are integrated on what is called a cartridge. The word cartridge designates new kinds of biochips with which microbiological tests in particular can be carried out.

Cartridges generally include a microfluidic system of cavities and channels which are necessary, for example, for breakdown of the sample, for cleaning the target molecules, and possibly for amplification and detection (on a microarray). Biochips of this kind can be miniaturized to a check card format and are also referred to by the expression "lab-on-a-chip". In the text below, the terms "biochip" and "cartridge" are used alongside one another and each designate a "lab-on-a-chip" of this kind.

It would be desirable to be able to use such a cartridge for different sample materials. However, this is not yet possible at present, since different procedures for sample breakdown are needed for different sample materials (for example blood, sputum, biopsies, etc., in the case of samples from humans). Depending on the aim of the test, different sample-processing steps are also needed:

To be able to detect certain intracellular or membrane-bound proteins or nucleic acids in blood or plasma, cell breakup (lysis) is required in the first instance, in order to free the desired target molecules and bring them into solution. For this purpose, only small amounts of blood are generally needed, for example if the aim is to detect human genes or ubiquitous proteins. By contrast, a more complicated type of sample-processing is necessary if the sample material is more compact, e.g. in the case of tissue samples from biopsies, if the cells are robust to chemical agents (e.g. *Mycobacterium tuberculosis*) of if they are present only in low concentration in the sample (e.g. HIV viruses or *Staphylococcus aureus* pathogens in urine). In samples of this kind, it is necessary to employ more aggressive chemical lysis reagents, higher temperatures, freeze/thaw cycles and, in some cases, mechanical methods in order to efficiently break up the cells and bring the target molecules into solution. For detection of low concentrations of viral and bacterial pathogens, large quantities of body fluid (>1 ml) have to be processed in order to obtain sufficient material for the subsequent analysis steps. In some cases, the concentration of the pathogens in the tissue sample would have to be increased. For this purpose, ultracentrifugation is used for example, or binding to matrices or resins (chromatographic methods).

Complicated sample-processing steps of this kind can presently only be carried out manually or semi-manually, although this is undesirable in routine clinical practice, on grounds of cost, and for reasons of reproducibility and risk of infection. Alternatively, different cartridges would have to be developed for different sample materials, or an extremely complex and large "universal cartridge" integrating all possible methods would have to be made available.

To avoid the problem of increasing the concentration of viral and bacterial pathogens, it would also be possible to process larger quantities of sample material, but this would again have the consequence of the size of the cartridge increasing and of the assay no longer being able to be carried out at check card size (for example, as in the EDD system from directif).

A particular problem arises when the same test has to be applied as standard to different sample materials. For example, a human genetic test can be carried out both with blood samples and with smear material. However, this requires a different input of the sample and a different processing of the sample. In the fully integrated systems known today, different cartridges would have to be produced for the same test. This would mean disadvantages in terms of production costs and of the work involved in the corresponding approval procedures.

SUMMARY

In at least one embodiment of the invention, a system permits sample-processing for different types of sample materials for the above-described lab-on-a-chip systems.

According to at least one embodiment of the invention, a module is used for processing a biological sample, the module including a hollow space and an interface at which the processing module can be connected to a cartridge with a miniaturized laboratory, in which cartridge the analysis steps necessary for the detection or quantifying of the target substance can be carried out.

According to at least one embodiment, this has the advantage that, for different sample materials, different processing modules can be used which, if appropriate, involve different functions and reagents that are adapted to a certain tissue type. All the processing modules can be connected to one and the same cartridge type which is then used to analyze the processed sample. In this way, one and the same cartridge can be used for different types of sample material (smears, lavage fluid, blood, etc.). A universal cartridge can also be used that is suitable for different applications.

The sample-processing includes, for example, the steps of concentration, extraction and/or multiplication of cells, in particular of viruses or bacteria, the steps of concentration, extraction and/or amplification of molecules, homogenization or liquefaction of the sample, cell lysis, or combinations of these steps.

The processing module is particularly preferably a vessel with, for example, a cylindrical hollow space. The latter preferably includes a narrowing, in particular funnel-shaped end, at the tip of which there is an opening acting as interface to the cartridge. In this way, after the sample has been processed, the processing module can be applied with the downwardly extending tip onto the cartridge, such that the sample is transferred into the latter by gravity. Alternatively, the processed sample can also be transferred by exchange of a fluid volume between module and cartridge, e.g. by way of the plunger described below.

According to an example embodiment, a displaceable plunger is also arranged in the hollow space, such that liquid samples in particular can be introduced by pulling the plunger back, in the manner of a medical syringe. The sample can pass into the processing module through the opening that is later to be connected to the cartridge. The plunger can also later be used, after the processing, to introduce the sample into the cartridge. In order to introduce samples in solid form, e.g. biopsies, the processing module can be provided with a closeable lid.

In an example embodiment, the extraction and/or the transfer of the sample into the cartridge can take place with the aid of spherules or "beads" which, on their surface, are provided with binding partners (for example monoclonal antibodies or oligonucleotides) of the target substance. The target substance can thus accumulate on the spherules and can be transferred with these into the cartridge. A liquid exchange between processing module and cartridge is not necessary in this case. Moreover, a concentration of the target substance takes place. The spherules can either be added to the sample before its introduction into the processing module, or they can already be present in the form of dry reagent or in solution or suspension in the hollow space. In the case of large samples of liquid, the target cells (for example bacteria) are bound by the spherules after an incubation time and further concentrated in subsequent steps.

The spherules are particularly preferably what are known as magnetic beads. Such magnetic beads preferably have an at least approximately spherical or elliptic shape and have a diameter of ca. 30-350 nm, in particular 50-310 nm, and particularly preferably ca. 110-220 nm. They can be produced, for example, according to the method described by Albrecht M. et al. in "Magnetic multilayers on nanospheres", nature materials, 2005, pages 1-4 (the entire contents of which are hereby incorporated herein by reference), that is to say can comprise a core of polystyrene and a magnetic or magnetizable coating, in particular of CoPb.

In at least one embodiment of the present invention, the use of magnetic beads has the advantage that the beads and the bound target substance can be transferred from the processing module to the cartridge by a magnetic field. In the subsequent analysis steps, the target substance can be freed from the magnetic beads, e.g. by denaturing, or can be analyzed together with the magnetic beads.

As has already been mentioned above, the geometry of the processing module and of the interface to the cartridge is also, in this embodiment, preferably chosen such that the cross section of the hollow space narrows continuously in the direction of the cartridge. This funnel shape avoids magnetic beads being moved by magnetic fields and/or by gravity into areas of the hollow space from which they cannot pass into the cartridge.

The magnetic field for driving the magnetic beads is generated, for example, by a permanent magnet or electromagnet, which is preferably arranged outside the processing module and the cartridge.

The interface between module and cartridge can include, for example, a fixed plug-type, bayonet-type or screw-type connection or a flexible tube connection.

With the interface, a fluidic connection between module and cartridge is preferably established which can be provided even before or during the processing phase and can also remain in place during the later analysis phase.

The processing module is particularly preferably a disposable article which, for example, can be made of suitable plastic or of glass.

For protection against contamination, the interface of the processing module is particularly preferably provided with a membrane or a partition wall which closes the module off in a leaktight manner as long as it is not connected to the cartridge. Similarly, the inlet opening of the cartridge can be provided with a further flexible membrane or partition wall. According to a particularly preferred embodiment, a spike is arranged on the inside of the membrane or partition wall in the processing module or in the cartridge, which spike pierces the membrane or partition wall upon attachment of the module to the cartridge and, in doing so, establishes a fluidic connection between module and cartridge.

The reagents required for the processing, for example lysis buffers, magnetic beads with nucleic acids and/or antibodies arranged on their surface, nutrients or solution buffers, are preferably stored in the processing module ready for use in a liquid or dry state, such that they mix automatically with the sample after the latter has been introduced.

For solid tissue samples (biopsies), mucous cell suspensions (smears) or viscous samples (sputum), additional mechanical elements or chemical agents are preferably provided in the processing module and are used to homogenize or liquefy the sample. Various techniques can be used to this end:

Preferably, an agitator is contained in the hollow space of the processing module and can be driven, for example in the manner of an electric motor, by externally applied magnetic fields. The agitator can, for example, contain a permanent magnet, or, alternatively, can be designed as the cage rotor of a three-phase asynchronous motor.

For homogenization of the sample, the agitator can further be equipped with blades which chop up a sample in the solid state.

To carry out incubations, the processing module can also include a heating element or can be heated from the outside.

At least one embodiment of the invention is further directed at a biochip kit which contains an above-described processing module and a cartridge with a miniaturized laboratory ("lab-on-a-chip") in which the analysis steps needed for the detection or quantifying of the target substance can be carried out, and which has an interface for connection of the processing module.

The biochip kit particularly preferably includes several processing modules which, in terms of their dimensions and/or in terms of other features, are each adapted to different sample materials.

It is also possible to provide several different cartridges that are suitable for carrying out different detection tests or quantifying tests. With this modular principle, a wide variety of different tests can be carried out with different sample materials.

Alternatively, or in addition to this, the biochip kit can also contain a universal cartridge which is suitable for many different applications (human genome, bacteriological, viral) and, by virtue of the different processing modules, is suitable for different sample materials.

Finally, at least one embodiment of the invention is directed at the use of the above-described processing module for processing of a biological sample for testing in a cartridge with a miniaturized laboratory ("lab-on-a-chip"), in which cartridge the analysis steps necessary for the detection or quantifying of a target substance can be carried out.

BRIEF DESCRIPTION OF THE DRAWINGS

The invention is now described in more detail on the basis of illustrative example embodiments and with reference to the attached drawings, in which:

FIG. 1 shows a schematic longitudinal section through a processing module according to a first embodiment of the invention;

FIG. 2 shows a schematic longitudinal section through a processing module according to a second embodiment of the invention;

FIG. 3 shows the processing module from FIG. 1 filled with magnetic beads;

FIG. 4 shows the processing module from FIG. 1 connected to a cartridge;

FIG. 5 shows a longitudinal section through an interface between processing module and cartridge, before connection;

FIG. 6 shows a longitudinal section through an interface between processing module and cartridge, after connection;

DETAILED DESCRIPTION OF THE EXAMPLE EMBODIMENTS

Figure 7:
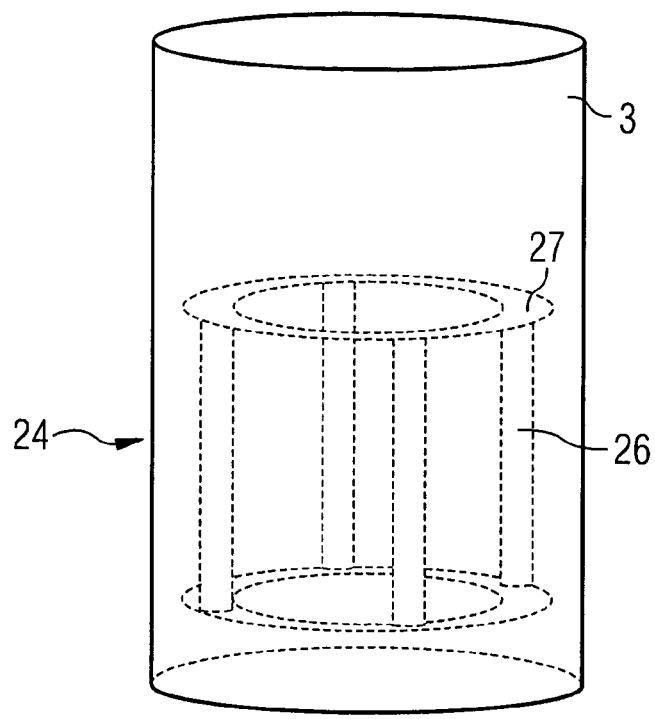
FIG. 7 shows a perspective view of an agitator according to a first embodiment.

It will be understood that if an element or layer is referred to as being "on", "against", "connected to", or "coupled to" another element or layer, then it can be directly on, against, connected or coupled to the other element or layer, or intervening elements or layers may be present. In contrast, if an element is referred to as being "directly on", "directly connected to", or "directly coupled to" another element or layer, then there are no intervening elements or layers present. Like numbers refer to like elements throughout. As used herein, the term "and/or" includes any and all combinations of one or more of the associated listed items.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

The terminology used herein is for the purpose of describing particular embodiments only and is not intended to be limiting of the present invention. As used herein, the singular forms "a", "an", and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Referencing the drawings, wherein like reference numerals designate identical or corresponding parts throughout the several views, example embodiments of the present patent application are hereafter described.

FIG. 1 shows a longitudinal section through a processing module 1 which includes an elongate hollow space 3. In the example shown, the latter is substantially cylindrical, with a longitudinal axis indicated by a dot-and-dash line. Alternatively, it can also have a spherical, ellipsoid or cylindrical shape with any area. In the lower part, the cross section of the hollow space narrows continuously in the direction of the opening 4. The transfer to the cartridge is made easier by this funnel-shaped portion 2. Arranged at the tip of the funnel, there is a tubular portion 5 which, together with the opening 4, forms the interface 14a to the cartridge. In order to introduce samples, the processing module is provided with a closeable lid 8.

In the alternative embodiment in FIG. 2, the sample is drawn up and/or discharged via the opening 4 with the aid of a plunger 6. The latter is displaceable in the manner of a medical syringe along the direction of the arrow P.

FIG. 3 shows an embodiment in which magnetic beads 10 are present in the hollow space 3 of the processing module 1. These magnetic beads 10 are used to bind the target substance, for example the target cells, if appropriate after an incubation time, and to concentrate them. Moreover, the transfer of the sample into the cartridge can be achieved by application of a magnetic field.

In FIG. 4, the processing module from FIG. 1 is shown while in fluidic connection with a cartridge 16. Here, the module is fitted with the interface 14a extending downward onto a corresponding interface 14b of the cartridge 16, such that the sample 12 can penetrate into the microfluidic system of the cartridge 16. If appropriate, further processing steps can take place inside the cartridge 16. The interface 14 can be configured as a plug-type, bayonet-type or screw-type connection.

A particular embodiment of the interface 14 is shown in FIGS. 5 and 6. In this embodiment, the tubular portion 5 leading to the opening 4 of the processing module is closed off by a flexible membrane or partition wall 20. The latter can be made of an elastomer material, for example. Viewed from the outside, a spike 18 is mounted behind the membrane or partition wall 20, and its tip is either embedded in the membrane or partition wall 20, as in the example shown, or touches the latter or is arranged at a slight distance from it. The spike 18 is provided with a hollow bore which is connected to the hollow space 3 of the processing module 1. This entire portion is designated as the interface 14a of the processing module. The corresponding interface 14b of the cartridge likewise has a tubular portion which is closed by a further flexible membrane or partition wall 22 that seals off the cartridge in a leaktight manner in the unconnected state. When the interfaces 14a and 14b are pressed onto one another in the direction of the arrows, the spike 18 pierces both membranes or partition walls and in doing so establishes a fluidic connection between processing module 1 and cartridge 16, as is shown in FIG. 6. The processed sample, e.g. molecules attached to magnetic beads, can thus pass from the hollow space 3 into the inlet opening of the cartridge.

After the processed sample has been transferred into the cartridge, the connection can, if appropriate, be undone. In doing so, the spike 18 of the processing module is withdrawn from both membranes and partition walls 20, 22, which then close again. In this case therefore, an undesired flow of liquids from the processing module or cartridge is also ruled out. The configuration of the spike 18 as a downward continuation of the hollow space 3 particularly advantageously permits a suitably funnel-shaped design of the latter, thereby ensuring that magnetic beads do not become caught during the emergence from the processing module.

Figure 8:
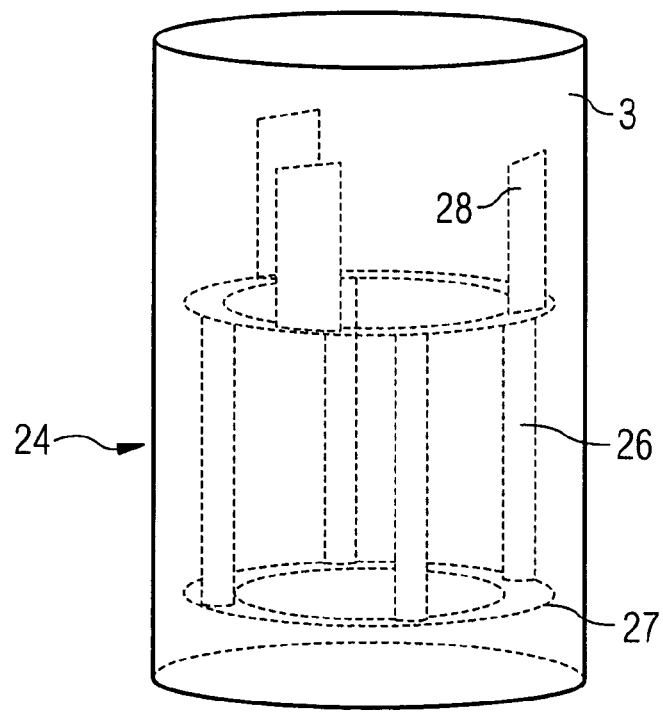
FIG. 8 shows a perspective view of an agitator according to a second embodiment.

To ensure that the sample and, if appropriate, reagents are able to react optimally with one another in the hollow space 3, the module can be shaken manually or by machine before the analysis assay is performed in the cartridge. FIGS. 7 and 8 therefore show embodiments in which an agitator 24 is present in the hollow space of the processing module.

The agitator body 24 shown in FIG. 7 is designed in the manner of a cage rotor of a three-phase asynchronous motor. For this purpose, it has several leads 26 which are oriented in the longitudinal direction and are connected at the end faces by an annular lead 27. These elements are preferably made of conductive material, e.g. copper or aluminum. In a cage rotor of this kind, an external, rotating magnetic field is used to induce currents, which in turn result in further magnetic fields and thus generate a torque in the cage rotor 24. Alternatively, the rotor can also be completely or partially filled with conductive metal, in which case too the torque is generated by eddy currents to the conductive material. In both cases, the agitator 24 is preferably coated such that the leads do not influence the chemical reactions taking place in the interior of the processing module. In the example in FIG. 7, the leads 26 oriented in the longitudinal direction are at the same time used to agitate the sample.

Alternatively, the agitator 24 can also be provided with one or more permanent magnets, likewise set in rotation by externally applied rotating magnetic fields.

According to FIG. 8, the function of the agitator can be extended by providing it with one or more blades 28. These blades can chop up a sample in the solid state. In conjunction with suitable pre-stored solution buffers, a homogenization of the sample can be achieved in this way.

The rotating magnetic fields are preferably generated externally. For this purpose, the processing module 1 and the cartridge 16 can additionally be assigned a sample-processing device 30 through which, for example, the reactions inside the cartridge can also be controlled. For this purpose, an electronic module can be provided, if appropriate with attached monitor, keyboard, mouse and/or attached PC.

Figure 9:
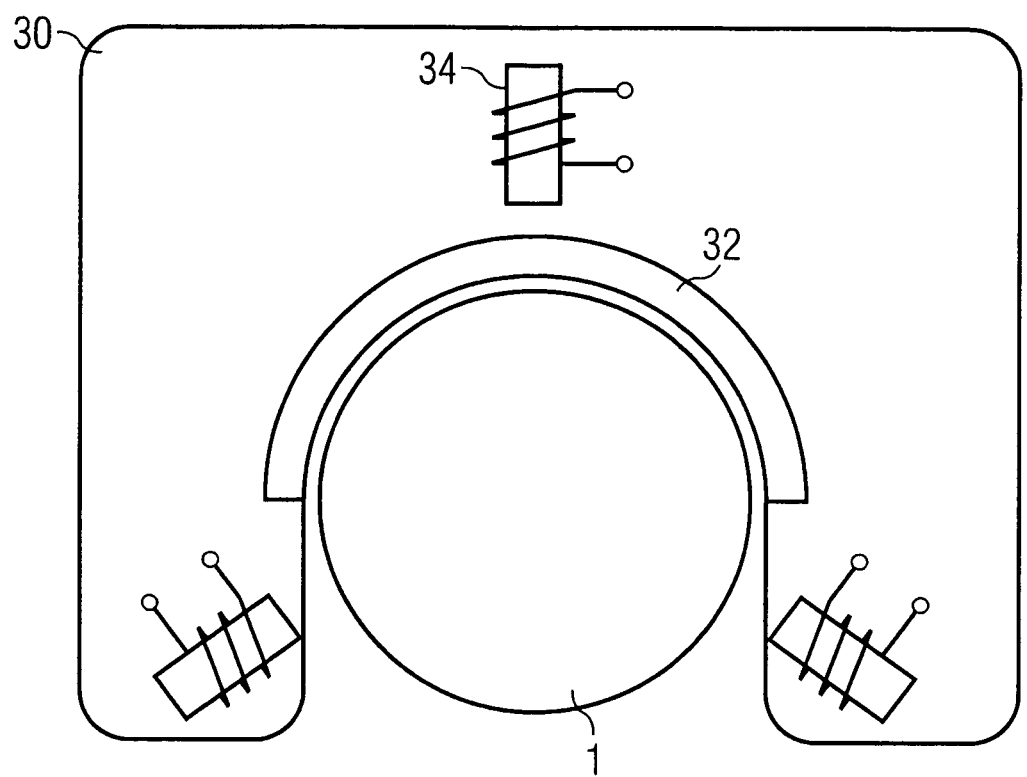
FIG. 9 shows a cross section through a processing module and an associated sample-processing device.

An illustrative embodiment of a sample-processing device 30 of this kind is shown in FIG. 9. The device has an insert bay for the processing module 1, the latter being inserted therein before the assay is carried out. In the insert bay, the processing module 1 is optionally enclosed by a heating element 32. Heating of this kind can promote biochemical processes, for example the breakup of cell membranes and conglomerates (for example, liquefaction of sputum). The incubation of liquids (blood, urine, cerebrospinal fluid) for the purpose of enrichment or multiplication of pathogens that are present only at a low concentration has proven particularly advantageous. This pre-incubation in the processing module 1 replaces an external primary culture. After a defined incubation time, the sample material can be further processed automatically in the processing module 1 or in the cartridge 16. If a pre-defined pathogen concentration is needed in the culture medium, the process can be monitored visually, e.g. by nephelometry or turbidimetry.

The sample-processing device shown in FIG. 9 is also provided with electromagnets 34 for generating a rotating magnetic field with which an agitator 24 or an associated rotor in the processing module can be rotated.

At least one embodiment of the invention described has the advantage that greater sample volumes can be processed than would be previously possible on a cartridge. The cartridge can be designed simply and thus in miniaturized form, since no additional chambers, fluid channels or plungers and valves have to be accommodated thereon in order to permit complex sample-processing.

In the processing module, the same media can be used as are also employed for further processing in the cartridge, in particular magnetic beads.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A module for processing a biological sample for a test in which a target substance in the sample is at least one of detected and quantified, the processing module comprising:
   a hollow space, wherein the hollow space includes a narrowing having an first opening at a tip of the narrowing;
   a displaceable plunger arranged in the hollow space, the displaceable plunger being configured to draw up the biological sample;
   at least one of a first membrane and a first partition wall that seals of the first opening in a leaktight manner when a cartridge with a miniaturized laboratory is not connected to the processing module, and that allows a fluidic connection between the cartridge and the processing module when the cartridge is connected to the processing module; and
   a first interface at which the processing module is connectable to the cartridge with the miniaturized laboratory, the cartridge including,
      a plurality of channels configured to perform analysis steps for the at least one of detection and quantification of the target substance, and
      a second interface including a second opening sealed by at least one of a second membrane and a second partition wall,
   wherein the cartridge with the miniaturized laboratory is one selected from a biochip miniaturized to a check card format and a lab-on-chip,
   an inside of the at least one of the first membrane and the first partition wall includes a spike adapted to pierce the at least one of the second membrane and the second partition wall upon connection of the processing module to the cartridge, and
   the first interface is connected to the hollow space.

2. The processing module as claimed in claim 1, wherein the cartridge is configured to enable
   at least one of concentration, extraction and multiplication of cells, at least one of concentration, extraction and amplification of molecules, at least one of homogenization and liquefaction of the sample, cell lysis, and combinations thereof.

3. The processing module as claimed in claim 1, wherein the hollow space contains spherules which, on their surface, are provided with binding partners of the target substance.

4. The processing module as claimed in claim 3, wherein the spherules are magnetic beads which, by way of a magnetic field, are transferable from the processing module through the first interface into the cartridge.

5. The processing module as claimed in claim 3, wherein the first interface is configured to transfer the spherules, when the processing module is connected to the cartridge, in order to transfer the processed sample from the processing module to the cartridge.

6. The processing module as claimed in claim 1, wherein the first interface is adapted to permit at least one of a plug-type, screw-type, tube-type and bayonet-type connection to the cartridge.

7. The processing module as claimed in claim 1, wherein the spike is adapted to establish a connection between the cartridge and the processing module.

8. The processing module as claimed in claim 1, wherein reagents necessary for processing are stored in the processing module in a liquid or dry state.

9. The processing module as claimed in claim 1, wherein, when connecting the processing module to the cartridge, a fluidic connection is established for transferring the processed sample from the processing module to the cartridge.

10. A method, comprising:

using the processing module as claimed in claim 1 for processing the biological sample for the test in the cartridge with the miniaturized laboratory, wherein the analysis steps necessary for the at least one of detection and quantifying of a target substance are carried out in the cartridge.

11. The processing module as claimed in claim 1, wherein the hollow space comprises a funnel-shaped end.

12. The processing module as claimed in claim 1, further comprising a seal at the first opening of the narrowing, wherein the tip of the narrowing is at least one of embedded within or contacting the seal.

13. The processing module as claimed in claim 1, further comprising an agitator in the hollow space.

14. The processing module as claimed in claim 13, wherein the agitator is drivable by externally applied magnetic fields.

15. The processing module as claimed in claim 14, wherein the agitator has cutting blades for homogenization of the sample.

16. The processing module as claimed in claim 14, wherein the agitator is additionally provided with cutting blades for homogenization of the sample.

17. The processing module as claimed in claim 1, wherein the narrowing of the hollow space includes a tubular portion extending past and enclosing the tip and the first opening in the tip is closed by the at least one of the first membrane and the first partition extending between sidewalls of the tubular portion.

18. The processing module as claimed in claim 17, wherein the first interface of the cartridge includes a sidewall extending from a surface of the cartridge and the sidewall is configured to interface with the tubular portion to provide a physical connection between the cartridge and the hollow space.

19. The processing module as claimed in claim 1, wherein the processing module is configured to process a larger volume of the biological sample than the cartridge.

20. The processing module of claim 1, wherein the at least one of the first membrane and the first partition wall is configured to surround the tip of the narrowing, when the processing module is connected to the cartridge.

* * * * *